(12) United States Patent
Takeda

(10) Patent No.: US 8,315,354 B2
(45) Date of Patent: Nov. 20, 2012

(54) DYNAMIC RADIOGRAPHING SYSTEM

(75) Inventor: Yoshihiro Takeda, Hachioji (JP)

(73) Assignee: Konica Minolta Medical & Graphic, Inc. (JP)

( * ) Notice: Subject to any disclaimer, the term of this patent is extended or adjusted under 35 U.S.C. 154(b) by 235 days.

(21) Appl. No.: 12/745,833

(22) PCT Filed: Nov. 19, 2008

(86) PCT No.: PCT/JP2008/071007
§ 371 (c)(1),
(2), (4) Date: Jun. 2, 2010

(87) PCT Pub. No.: WO2009/072397
PCT Pub. Date: Jun. 11, 2009

(65) Prior Publication Data
US 2010/0254512 A1     Oct. 7, 2010

(30) Foreign Application Priority Data

Dec. 7, 2007 (JP) ................................ 2007-317443
Dec. 7, 2007 (JP) ................................ 2007-317449

(51) Int. Cl.
*G01N 23/04* (2006.01)
*G06K 9/00* (2006.01)

(52) U.S. Cl. ........................................ 378/62; 382/132
(58) Field of Classification Search ............... 378/4, 19, 378/25, 62, 95; 382/130, 132; 345/635
See application file for complete search history.

(56) References Cited

U.S. PATENT DOCUMENTS

| 7,590,270 | B2 * | 9/2009 | Asbeck et al. ............... 382/128 |
| 7,689,261 | B2 * | 3/2010 | Mohr et al. .................... 600/407 |
| 2005/0002549 | A1 | 1/2005 | Nay et al. |
| 2005/0015006 | A1 * | 1/2005 | Mitschke et al. ............ 600/431 |
| 2008/0292609 | A1 * | 11/2008 | Camus et al. .................. 378/21 |

FOREIGN PATENT DOCUMENTS

| DE | 10357274 A1 | 6/2004 |
| FR | 2848093 A1 | 6/2004 |
| JP | 11-76233 A | 3/1999 |
| JP | 2002-306483 A | 10/2002 |
| JP | 2003-265480 A | 9/2003 |
| JP | 2004-188196 A | 7/2004 |
| JP | 2004-337289 A | 12/2004 |

OTHER PUBLICATIONS

International Search Report for Application No. PCT/JP2008/071007 with English translation mailed Feb. 24, 2009.

* cited by examiner

*Primary Examiner* — Irakli Kiknadze
(74) *Attorney, Agent, or Firm* — Cantor Colburn LLP

(57) ABSTRACT

A dynamic radiographing system enables determination of an evaluation value of the heart function of a subject by plain radiography. The dynamic radiographing system comprises a radiographing apparatus, an image processing apparatus, and a console for diagnosis. The radiographing apparatus dynamically radiographs the heart of a subject and creates radiographs in plural time phases (Step S1). The image processing apparatus calculates an evaluation value of the heart function by using the radiographs in plural time phases (Step S4). The console for diagnosis displays information on the calculated evaluation value on the display section (Step S5).

12 Claims, 12 Drawing Sheets

DYNAMIC RADIOGRAPHING SYSTEM

CROSS REFERENCE TO RELATED APPLICATIONS

This is a U.S. national stage of application No. PCT/JP2008/071007, filed on 19 Nov. 2008. Priority under 35 U.S.C. §119(a) and 35 U.S.C. §365(b) is claimed from Japanese Application No. 2007-317443, filed 7 Dec. 2007, and from Japanese Application No. 2007-317449, filed 7 Dec. 2007, the disclosures of which are also incorporated herein by reference.

FIELD OF THE INVENTION

The present invention relates to a dynamic radiographing system.

BACKGROUND OF THE INVENTION

Various forms of measurement have been performed to know the state of the heart function. For example, a measuring system is disclosed by which the blood speed and blood pressure are calculated from the cross sectional shape of a blood vessel using an ultrasound tomographic image, whereby the state of blood flow is grasped (Patent Literature 1 for example).

A calculating system is also disclosed by which the movement information showing the heart movement is calculated using the images in chronological order obtained by an ultrasonic wave, MRI (Magnetic Resonance Imaging) or CT (Computer Tomography), whereby the state of heart movement is grasped (Patent Literatures 2 and 3 for example).

MRI imaging CT radiography and catheter examination are used to examine the heart. However, these imaging apparatuses for examination are high-priced and increase the financial burden. The catheter examination requires the catheter to be inserted into a patient body. This is a heavy burden on the patient.

In addition to the imaging of MRI and CT, plain X-ray radiography is also commonly practiced. This requires imaging apparatuses for a plurality of types of imaging, which again raises cost problems. Further, a plurality of shooting operations must be performed by changing the apparatuses. This signifies a greater burden on the patient.

As a radiographing apparatus developed to solve these problems, a CT radiographing apparatus is used to perform both the CT radiographing and plain X-ray radiographing operations (Patent Literature 4 for example).

Patent Literature 1: Japanese Unexamined Patent Application Publication No. 11-76233
Patent Literature 2: Japanese Unexamined Patent Application Publication No. 2002-306483
Patent Literature 3: Japanese Unexamined Patent Application Publication No. 2003-265480
Patent Literature 4: Japanese Unexamined Patent Application Publication No. 2004-337289

DISCLOSURE OF INVENTION

Problems to be Solved by the Invention

However, the MRI and CT radiographing apparatuses are high-priced and increase the financial burden. At the time of examination, plain X-ray radiography is often performed. If a plurality of imaging operations by using ultrasonic wave or MRI are required in addition to such a basic radiography, a burden of the patient will be increased.

In small-sized medical institutions, plain X-ray radiographing apparatuses have come into more widespread use than the CT radiographing apparatuses. The methods disclosed in Patent Literature 4 cannot be adopted.

An object of the present invention is to obtain an evaluation value for heart function by a plain X-ray radiographing operation.

Another object of the present invention is to obtain an X-ray image suited to medical examination of the heart part by a plain X-ray radiographing operation characterized by reduced costs and burden on a patient.

Means for Solving the Problems

Preferred embodiments according to the invention are as follows.

(1) A dynamic radiographing system, which includes:
a radiographing device which further contains an X-ray source for emitting X-rays and a detector for detecting the X-ray emitted from the X-ray source, and which takes a dynamic radiograph of a heart part of a subject and generates X-ray images in a plurality of time phases;
an image analysis device for calculating the evaluation value relating to a heart function using the aforementioned X-ray images in a plurality of time phases;
a display device; and
a control device for permitting the information on the calculated evaluation value to be displayed on the display device.

(2) The dynamic radiographing system described in Item 1, wherein the aforementioned evaluation value contains that of the blood speed and
the image analysis device detects the image of a pulsating part from the X-ray images in a plurality of time phases, and calculates the center of gravity of the pulsating part detected from each of the X-ray images in a plurality of time phases, and then calculates the traveling distance of the center of gravity per unit time as the evaluation value of the blood speed.

(3) The dynamic radiographing system described in Item 1 or 2,
wherein the aforementioned evaluation value contains that of the cardiac output and
the image analysis device detects the image of a pulsating part from the X-ray images in a plurality of time phases and calculates the volume of the pulsating part having been detected, as the evaluation value for the cardiac output.

(4) The dynamic radiographing system described in any one of the aforementioned Items 1 through 3,
wherein the aforementioned evaluation value contains that of the beat and
the image analysis device detects the image of the main artery part from the X-ray images in a plurality of time phases and calculates a change of the signal value in a prescribed area of the main artery part detected from each of the X-ray images in time phases, as the evaluation value for the beat.

(5) The dynamic radiographing system described in any one of the aforementioned Items 1 through 4,
wherein the aforementioned evaluation value contains that of the distance, directionality or periodicity of the movement of the local part of heart and
the image analysis device detects the image of the heart part from the X-ray images in a plurality of time phases and calculates the distance, directionality or periodicity of the movement of the local part of heart between the images of the heart part having different time phases.

(6) The dynamic radiographing system described in Item 5, wherein the image analysis device calculates the evaluation values for the distance, directionality or periodicity of the movement of the local part of heart for each segment of the heart part.
(7) The dynamic radiographing system described in any one of the aforementioned Items 1 through 6, wherein the aforementioned control device allows at least one of the X-ray images in a plurality of time phases together with the information on the aforementioned evaluation value to be displayed on the display device.
(8) The dynamic radiographing system described in any one of the aforementioned Items 1 through 7, wherein the aforementioned radiographing device takes an enlarged radiograph of the heart part.
(9) The dynamic radiographing system described in any one of the aforementioned Items 1 through 8, wherein the aforementioned radiographing device takes a radiograph in the rotation angle phase in which the long axis of the heart part in the X-ray image is the longest.
(10) The dynamic radiographing system described in Item 1, which further includes:
a holding device for rotatably holding the subject as the radiographing target between the X-ray source and detector; and
a reading device for reading the X-ray image from the detector,
wherein, the control device controls the rotation angle phase of the holding device variably, allows X-rays to be emitted from the X-ray sources in a plurality of rotation angle phases in the pre-radiographing mode, and determines the rotation angle phase in which the long axis of the heart area is the longest, based on each of the X-ray images obtained from the detector by means of the reading device, in each of the rotation phases, and allows the X-rays to be emitted from the X-ray source while fixing the holding device at the rotation angle phase in the actual radiographing mode.
(11) The dynamic radiographing system described in Item 10, wherein the holding device is arranged movably between the X-ray source and detector, and the control device determines, in the pre-radiographing mode, the rotation angle phase in which the long axis of the heart area is the longest, at the position where the holding device has been moved to the detector side, and in the actual radiographing mode, allows the holding device to move to the X-ray source side after fixing the rotation angle phase of the holding device.
(12) The dynamic radiographing system described in Item 10 or 11,
wherein the control device allows X-rays to be emitted a plurality of times on a continuous basis from the X-ray source in the actual radiographing mode, and permits the X-ray image to be read from the detector by the reading device for each emission of the X-ray, whereby dynamic radiographing of the heart area is performed.
(13) The dynamic radiographing system described in any one of the Items 10 through 12, which further includes
an image processing device which applies image processing in conformity to the heart part to the X-ray image obtained by the actual radiographing operation.

Effects of the Invention

According to the embodiment described in Item 1, a doctor obtains an evaluation value relating to heart function by a plain X-ray radiographing operation and uses this value for diagnostic purpose. This can be achieved by using a widely used radiographing device for plain X-ray radiographing operation, without having to use a high-priced imaging apparatus such as an MRI, whereby cost reduction can be accomplished. Except for the X-ray radiographing operation performed at base, this method eliminates the need of another separate examination for inspection of the heart function, with the result that the patient burden is reduced.

According to the embodiment described in Item 2, the doctor can evaluate the blood speed.

According to the embodiment described in Item 3, the doctor can evaluate the cardiac output.

According to the embodiment described in Item 4, the doctor can evaluate the beat.

According to the embodiment described in Item 5, the doctor can evaluate the movement of the local part of heart.

According to the embodiment described in Item 6, the doctor can evaluate the movement of the local part of heart for each segment of the heart part. The reduction in the heart function by disease often represents the reduction in the function of the portion of the heart causing that disease, rather than the reduction in the entire heart function. The evaluation value for each segment provides effective diagnostic information.

According to the embodiment described in Item 7, the doctor evaluates the heart function while observing the X-ray image.

According to the embodiment described in Item 8, an enlarged X-ray image of the heart part can be obtained, and hence an X-ray image suited for diagnosis of the heart part is provided.

According to the embodiment described in Item 9, radiographing operation can be performed in the radiographing direction wherein the long axis of the heart part is the longest. This arrangement provides an X-ray image suited for diagnosis of the heart part.

According to the embodiment described in Item 10, the pre-radiographing operation assists the heart part to be radiographed from the direction that ensures easiest observation, and thereby an X-ray image suited for diagnosis is provided. Since the normal plain X-ray radiography is used, the burden on the patient is reduced and this invention can be used in the radiographing apparatus for plain X-ray radiography widely used in medical institutions. This invention provides an X-ray image suited for medical examination of the heart part without increasing the cost.

According to the embodiment described in Item 11, a distance is placed between the subject and detector, whereby an enlarged image of the heart part can be obtained. Thus, a doctor is provided with an X-ray image that ensures easy medical examination.

According to the embodiment described in Item 12, X-ray image in each time phase can be obtained by dynamic radiographing. The image supplies the doctor with information of temporal and dynamic changes.

According to the embodiment described in Item 13, image processing in conformity to the heart part can be applied, as exemplified by gradation processing by which the contrast of the heart part is enhanced. Thus, a high-quality X-ray image suited to the diagnosis of the heart part can be provided.

DESCRIPTION OF REFERENCE NUMERALS

Figure 1:
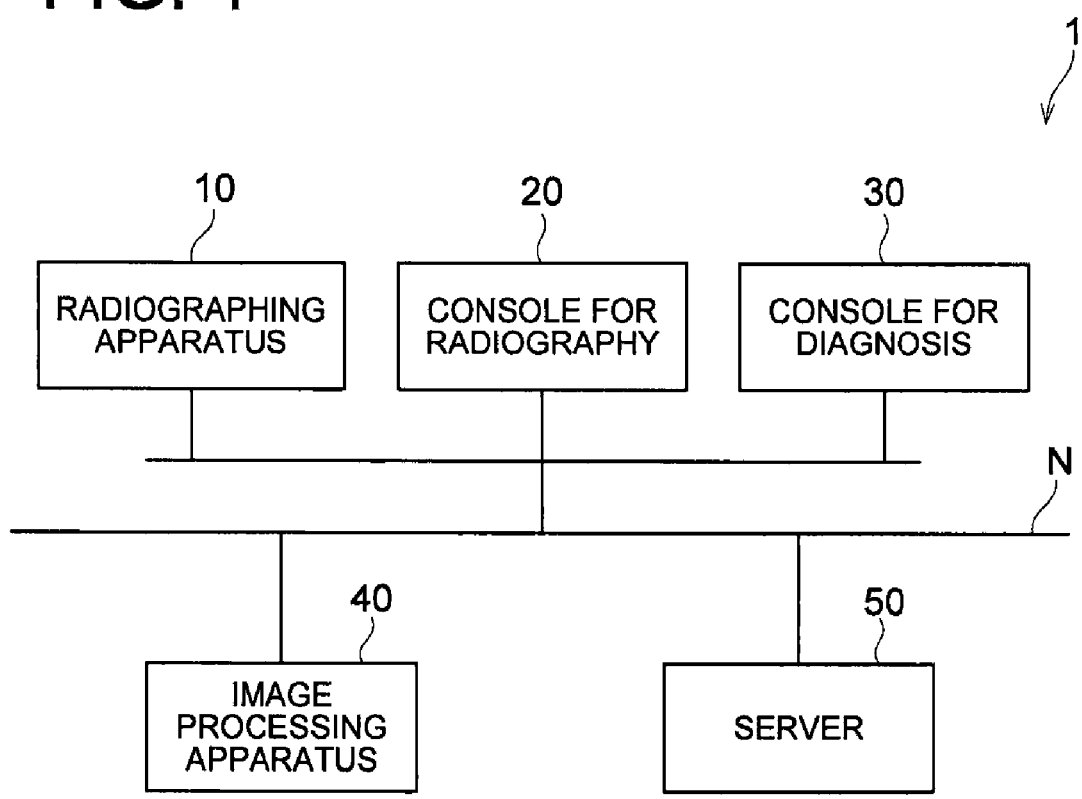
FIG. 1 is a diagram representing a dynamic radiographing system in the present embodiment

1. Dynamic radiographing system
10. Radiographing apparatus
11. X-ray source
12. Detector
13. Holding section
15. Cycle detecting section
16. Reading section
17. Drive section
20. Console for radiography
21. Control section
30. Console for diagnosis
40. Image processing apparatus
47. Image analysis section
50. Server

BEST FORM OF EMBODIMENT OF THE PRESENT INVENTION

The following describes the structure. FIG. 1 is a diagram representing a dynamic radiographing system 1 in the present embodiment. As shown in FIG. 1, the dynamic radiographing system 1 includes a radiographing apparatus 10, console for radiography 20, console for diagnosis 30, image processing apparatus 40 and server 50. These components 10 through 50 are connected via the network N.

The radiographing apparatus 10, console for radiography 20 and console for diagnosis 30 are used to radiograph the X-ray image of a subject. The radiographing apparatus 10 applies X-rays to the subject and reads the X-ray image from the detector. The radiographing apparatus 10 allows the dynamic radiographing to be performed. Dynamic radiographing can be defined as a method of radiography to obtain X-ray images in a plurality of time phases by continuous X-ray emission. The console for radiography 20 is used for operation by a radiographing technician to control irradiation of X-rays and reading of the X-ray image. The console for radiography 20 also displays the X-ray image having been read, to be checked by the radiographing technician (checked as to whether the image can be sent for the diagnosis in the next process or requires re-radiography). The console for diagnosis 30 is operated by the doctor to display the X-ray image sent from the console for radiography 20 for the diagnosis of the doctor.

Figure 2:
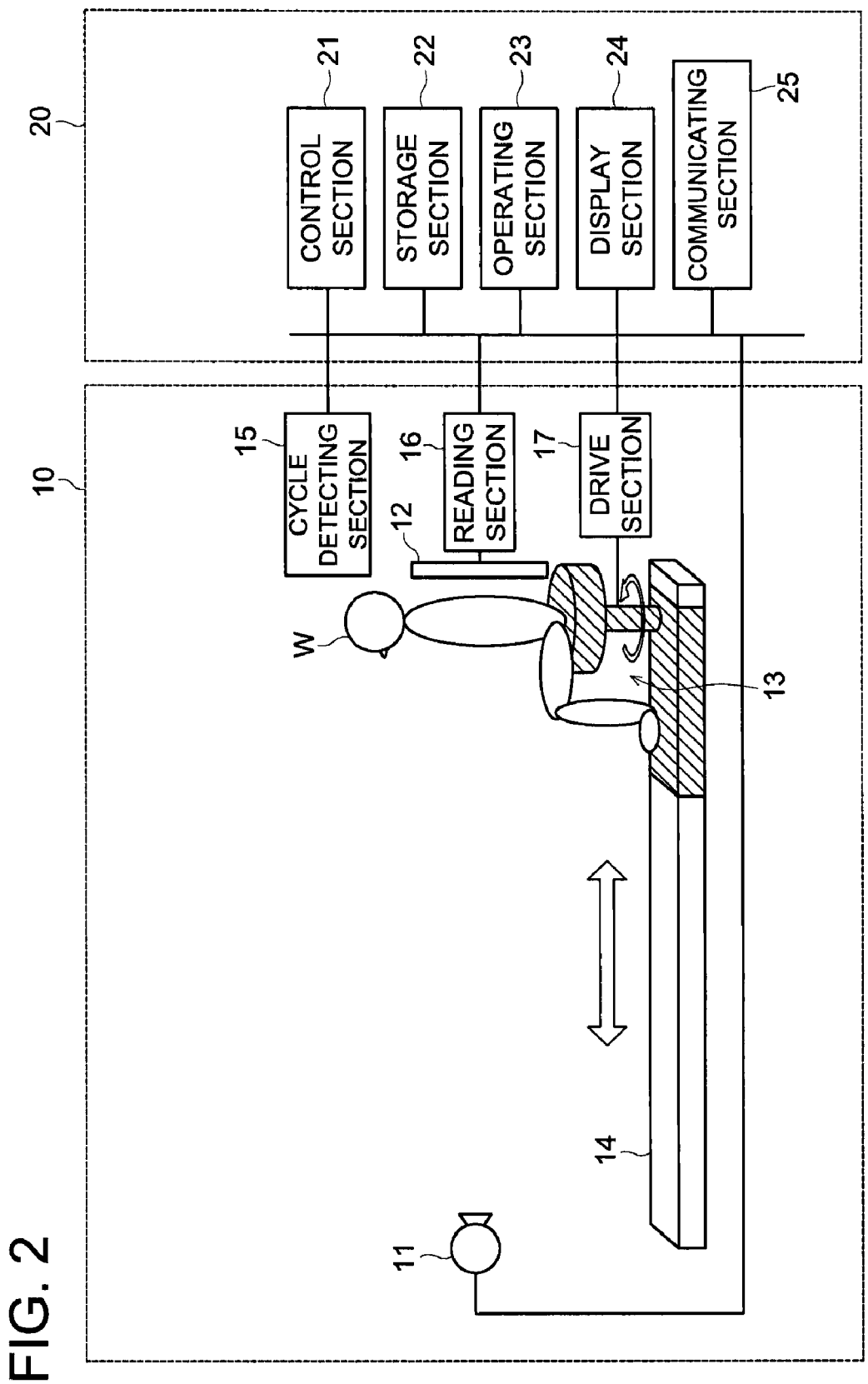
FIG. 2 is a diagram representing a functional structure of the radiographing apparatus and console for radiography of FIG. 1.

Referring to FIG. 2, the following describes the radiographing apparatus 10 and console for radiography 20. As shown in FIG. 2, the radiographing apparatus 10 includes an X-ray source 11, detector 12, holding section 13, traveling rail 14, cycle detecting section 15, reading section 16 and drive section 17. The console for radiography 20 includes a control section 21, storage section 22, operating section 23, display section 24 and communicating section 25. The X-ray source 11, cycle detecting section 15, reading section 16 and drive section 17 of the radiographing apparatus 10 are connected to the console for radiography 20.

The following describes the radiographing apparatus 10. The X-ray source 11 applies X-rays under the control of the control section 21 of the console for radiography 20. The X-ray irradiation conditions to be controlled include the pulse rate, pulse width, pulse intervals, irradiation start/end timing, X-ray tube current, X-ray tube voltage and filter values in the continuous radiographing mode of the dynamic radiographing operation. The pulse rate can be defined as the number of radiographing operations per unit time. The pulse width refers to the X-ray irradiation time per one radiographing operation. The pulse interval is the time, in the continuous radiographing mode, from the start of X-ray irradiation in a certain radiographing operation to the start of X-ray irradiation in the next radiographing operation.

The detector 12 is arranged opposed to the X-ray source 11, with a subject W sandwiched in-between. The detector 12 is exemplified by the FPD (Flat Panel Detector) in which X-ray detecting sensors are arranged in the form of a matrix. To be more specific, the X-rays are converted into the electric signals conforming to the intensity thereof, and are accumulated for each pixel (detecting sensor). Thus, the X-ray image is recorded by the detector 12.

The reading section 16 is a reading device to read the X-ray image from the detector 12. The reading section 16 sends the read X-ray image to the console for radiography 20. The reading operation is controlled by the control section 21. The image reading conditions to be controlled includes the frame rate, frame interval, pixel size and image size. The frame rate and frame interval are synonymous with the aforementioned pulse rate and pulse interval.

The holding section 13 is a holding device for holding the subject W as a target to be radiographed, and for fixing the radiographing position. FIG. 2 shows an example of a stool type as the holding section 13. A bed or other forms of devices can also be used as the holding section 13. The holding section 13 is arranged rotatably with the subject W held thereby. The drive section 17 drives the rotation of the holding section 13 under the control of the control section 21 of the console for radiography 20.

The holding section 13 is arranged movably between the X-ray source 11 and detector 12 by the traveling rail 14. To be more specific, the traveling mil is laid on the line between the X-ray source 11 and detector 12, and the holding section 13 is mounted so that the holding section 13 can slide on the traveling rail 14. This structure ensures that the holding section 13 moves freely between the X-ray source 11 and detector 12. It is also possible to make such arrangements that the movement of the holding section 13 is driven by the drive section 17 under the control of the control section 21, or by the radiographing technician.

The cycle detecting section 15 detects the cycle of the biological reaction at the radiographed area of the subject W. For example, when the radiographed position is the heart part, the cycle detecting section 15 detects the heart beat cycle using a heart rate meter or electrocardiograph. When the radiographed area is the chest including the lung field, the breathing cycle is detected using a breathing monitoring belt, CCD camera, optical camera, spirometer and others. The detected cycle information is outputted to the control section 21 of the console for radiography 20.

The following describes the console for radiography 20. The control section 21 includes a CPU (Central Processing Unit), RAM (Random Access Memory) and other. The control section 21 reads out the various programs stored in the storage section 22 by the CPU, and develops the programs in the RAM. Through collaboration with the developed programs, the control section 21 performs various forms of calculation and provides a centralized control of the operations of each component for processing.

The storage section 22 is a storage device such as a hard disk and stores various forms of programs used by the control section 21 and the parameter required to execute these programs. For example, the storage section 22 stores the radiographing conditions (e.g., X-ray image irradiation conditions and X-ray image reading conditions) optimized for each radiographing area.

The operating section 23 includes the keyboard, mouse and others. The operating section 23 generates the operation signal in response to these operations, and outputs this signal to the control section 21.

The display section 24 includes a display and displays various operation screens and X-ray image obtained by radiographing operation, under the display control of the control section 21.

The communicating section 25 has a communication interface and communicates with the external apparatus connected to the network N.

The console for diagnosis 30 is used for operations by the doctor, and displays the X-ray image sent from the console for radiography 20 so that this image is checked by the doctor. The basic structure of the console for diagnosis 30 is the same as that of the console for radiography 20. The console for diagnosis 30 includes a control section, operating section, display section, storage section and communicating section.

The image processing apparatus 40 and server 50 are used to provide the X-ray image obtained by radiographing to be diagnosed by the doctor.

Figure 3:
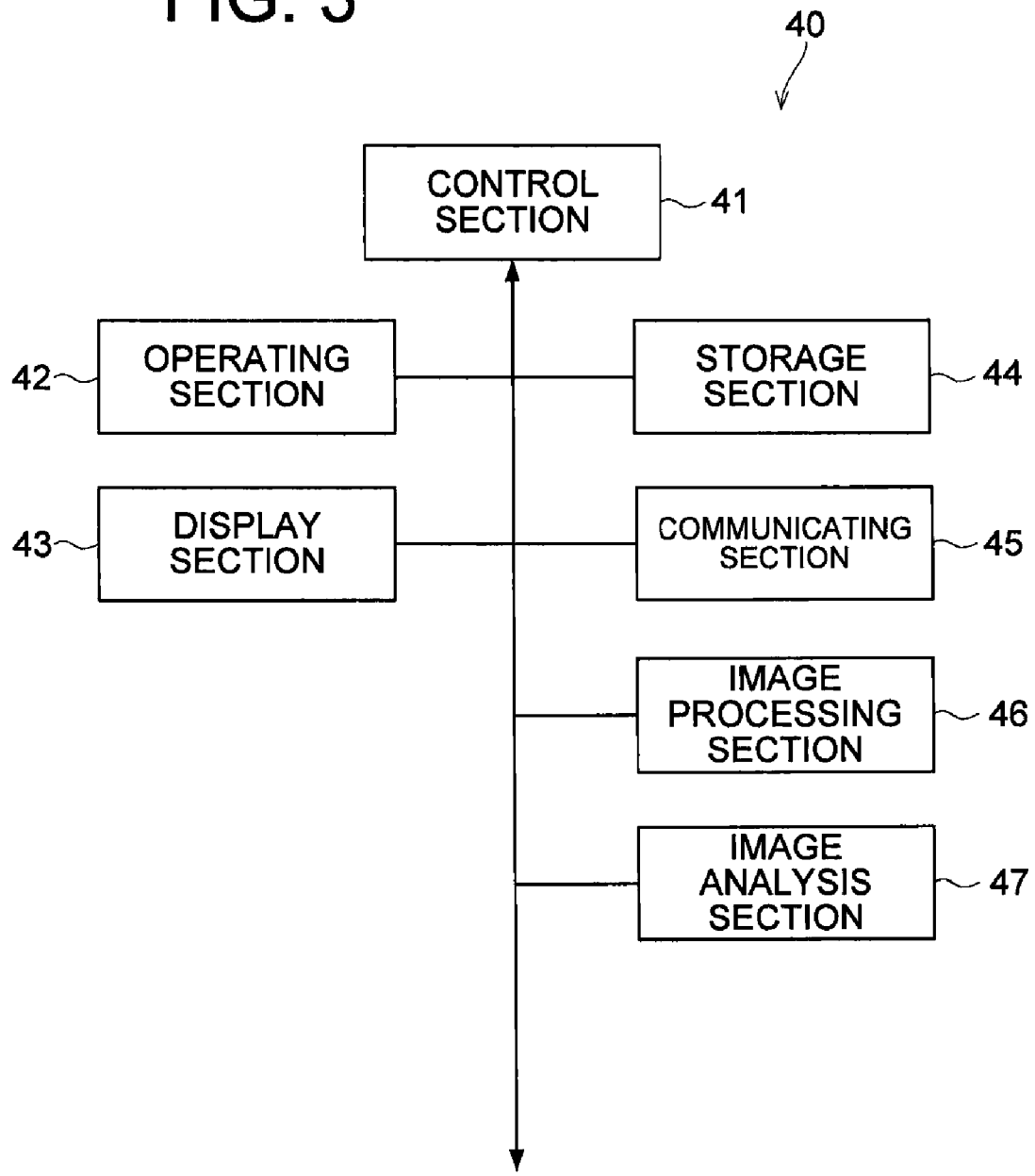
FIG. 3 is a diagram representing a functional structure of the image processing apparatus of FIG. 1.

Referring to FIG. 3, the following describes the image processing apparatus 40: The image processing apparatus 40 applies image processing to the X-ray image for an image quality of easy diagnosis. As shown in FIG. 3, the image processing apparatus 40 includes a control section 41, operating section 42, display section 43, storage section 44, communicating section 45, image processing section 46 and image analysis section 47.

The basic functions of the control section 41 through communicating section 45 are the same as those of the control section 21 through communicating section 25 of the console for radiography 20 described above, and will not be described in detail.

The image processing section 46 is an image processing device which applies various forms of image processing such as gradation conversion processing and frequency adjustment processing to the X-ray image. Image processing is executed through collaboration with the image processing program and CPU. The image processing of the type in conformance to the radiographed area is provided under the image processing conditions in conformance to the radiographed area. Details will be described later. The X-ray image subjected to the image processing is sent to the server 50 through the communicating section 45.

The image analysis section 47 analyzes the X-ray images in a plurality of time phases obtained from the heart part being dynamically radiographed, and calculates the evaluation values for heart function. The evaluation values for heart function include the evaluation values for blood speed, cardiac output, beat, and the distance, directionality or periodicity of the movement of the local part of heart. The specific method for calculating evaluation values will be described later.

The server 50 has large-capacity memory and in the memory, stores and manages the X-ray image having been subjected to image processing by the image processing apparatus 40. The X-ray image stored in the server 50 is distributed in response to the request by the console for diagnosis 30, and is utilized for diagnosis.

The First Embodiment

Figure 4:
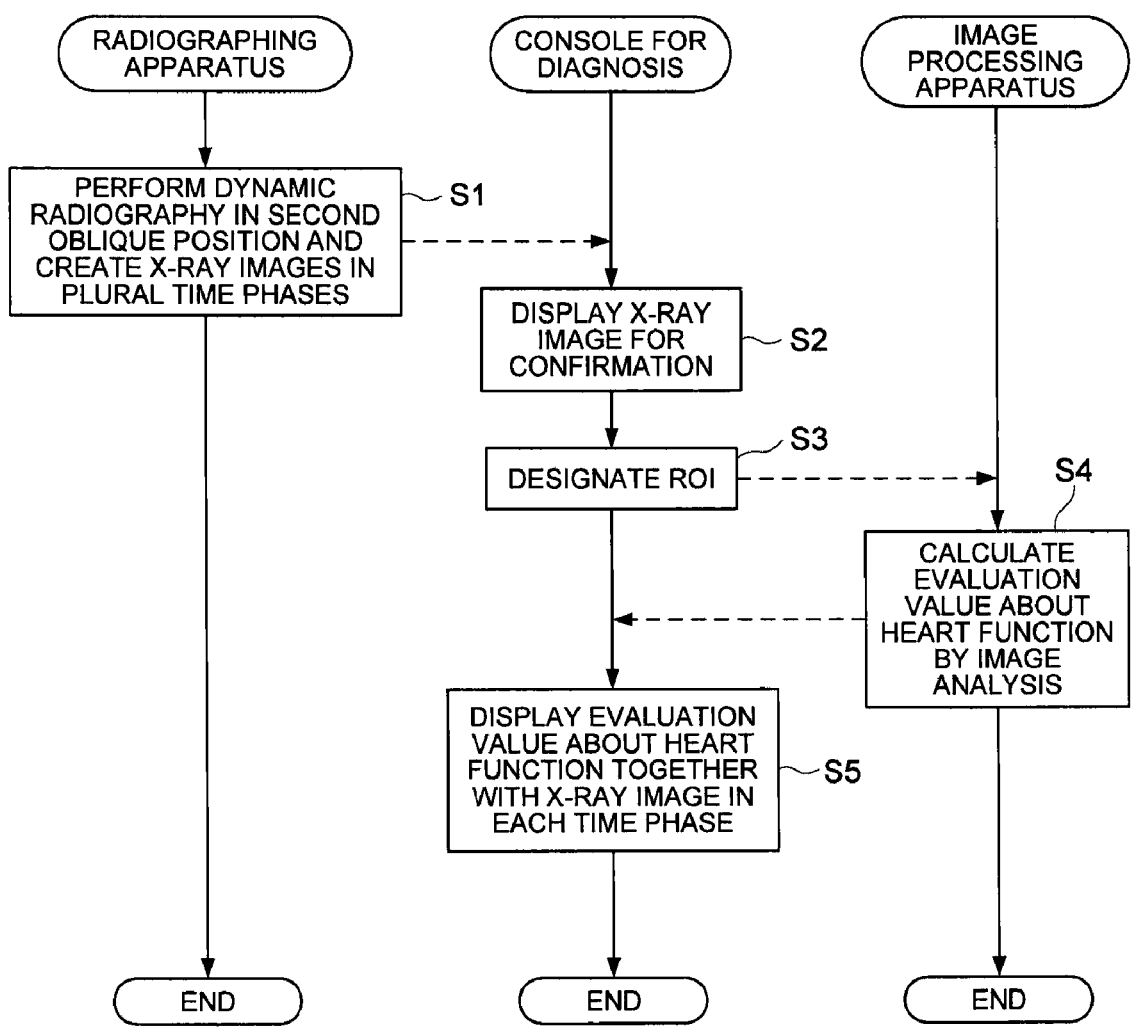
FIG. 4 is a diagram representing a flow of processing in the dynamic radiographing system.

The following describes the operation in the first embodiment. The first dynamic radiographing system 1 of the first embodiment takes a dynamic radiograph of the heart part, and calculates and displays the evaluation value for heart function, using the X-ray images in a plurality of time phases having been obtained. FIG. 4 is a diagram representing a flow of processing in the radiographing apparatus 10, console for diagnosis 30 and image processing apparatus 40 of the dynamic radiographing system 1 in the first embodiment.

As shown in FIG. 4, the heart part of the subject W is dynamically radiographed at the second oblique position in the radiographing apparatus 10, whereby the X-ray images at a plurality of time phases are generated (Step S1). Dynamic radiography is performed by magnification radiographing method. At the time of radiographing, the radiographing technician inputs the patient information on the subject W and specifies the radiographed area "HEART" using the operating section 23 of the console for radiography 20.

The second oblique position can be defined as a position in which the subject W is tilted with respect to the surface of the detector 12 in such a way that the left side of the body of the subject W comes closer to the X-ray source 11. The direction of the long axis of the heart is tilted with respect to the direction of the long axis of the body. If radiography is performed from the direction used in the case of radiographing the chest part, i.e., from straight ahead of the body, the long axis of the heart section cannot be maximized in the radiograph.

Figure 5:
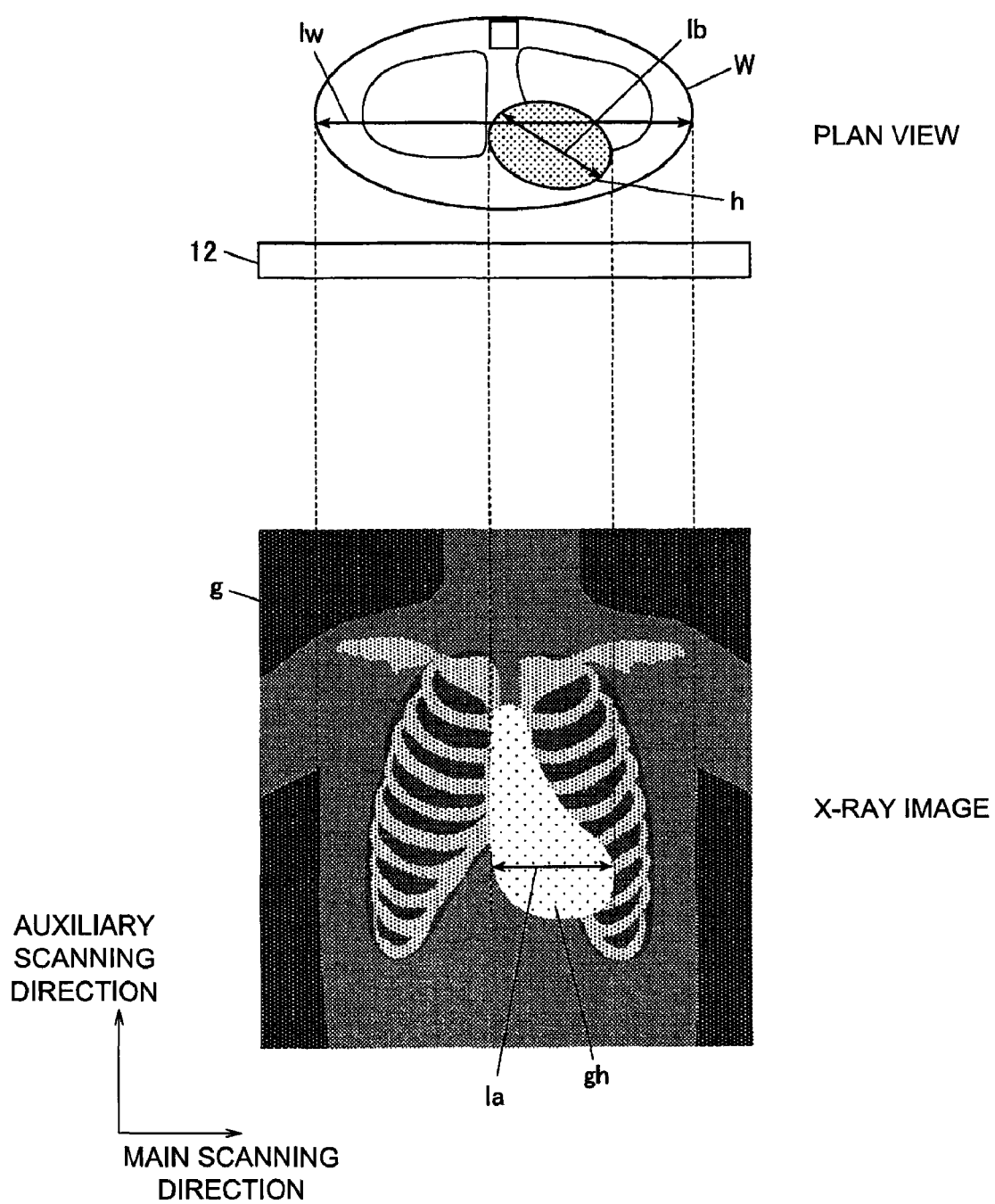
FIG. 5 is a diagram representing the relationship between the heart part and the image of the heart part in an X-ray image.

The following description refers to FIG. 5. FIG. 5 is a diagram representing the relationship between the top view of the subject W and detector 12, and the X-ray image "g" obtained by the detector 12. In FIG. 5, the subject W faces the detector 12.

As shown in FIG. 5, the heart part "h" is approximately elliptical, as viewed from the top. When the long axis $1b$ of the ellipse is maximized, i.e., when the long axis $1a$ of the heart part "gh" appearing on the X-ray image "g" is maximized, the ventricle of the heart is captured from the direction in which the long axis is maximized, and the dynamic state of the heart can be measured with the highest precision. However, the long axis $1b$ of the heart part "h" is not parallel with the long axis $1w$ of the body portion of the subject W. An X-ray image that ensures easier observation of the heart part cannot be obtained, if the radiographing operation is performed by making the surface of the detector 12 to be parallel with the long axis 1w of the body portion of the subject W, as in the case of the normal chest radiography.

To solve this problem, the subject W is rotated, and radiographing operation is performed at the rotation angle phase where the long axis 1b of the heart part "h" is maximized with respect to the detector 12, i.e., at the rotation angle phase where the long axis 1a of the heart part "gh" in the X-ray image "g" is maximized. The second oblique position is found in the radiographing direction in this case.

Figure 6:
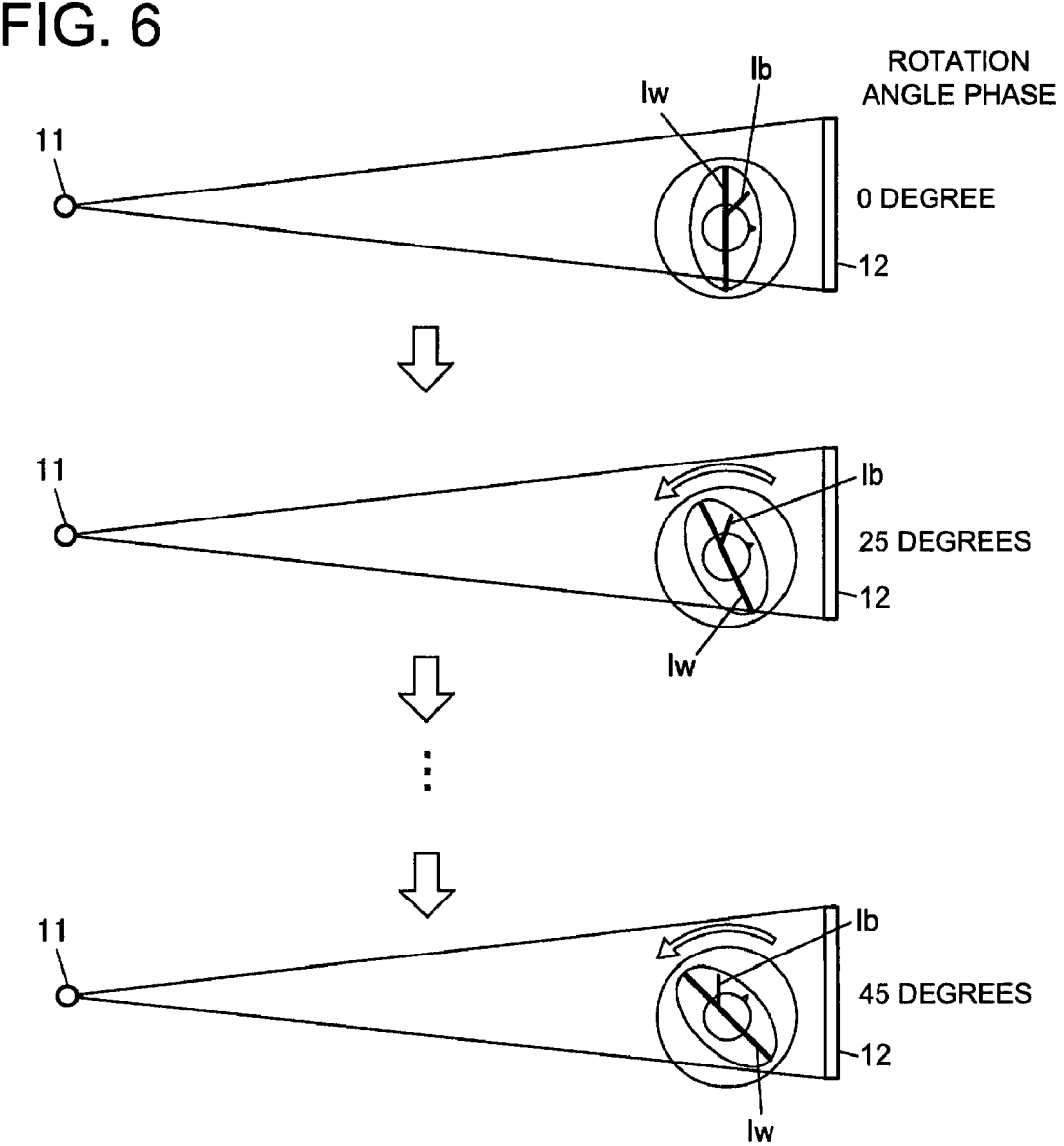
FIG. 6 is a diagram representing the relationship among the X-ray source, subject and detector in the pre-radiographing mode.

Thus, pre-radiographing is performed in advance to determine the rotation angle phase as the second oblique position. In the pre-radiographing operation, as shown in FIG. 6, the holding section 13 is given a prescribed angled turn several times when the subject W is sitting on the holding section 13. Radiographing is performed at every turn, thereby obtaining the rotation angle phase of the holding section 13 wherein the long axis 1a of the heart part "gh" appearing on the X-ray image "g" is maximized.

The rotation angle phase for pre-radiographing is obtained by determining the range of the average rotation angle phase where the long axis 1b of the heart part "h" is approximately parallel to the surface of the detector 12. The rotation angle phases for pre-radiographing are finely set within this range.

The radiographing technician allows the subject W to be seated on the holding section 13. In this case, the subject W is positioned so as to be close to the detector 12. Further, the subject W is fixed to the holding section 13 in such a way that the heart part of the subject W is located approximately at the center of the surface of the detector 12, in other words, the centerline of the X-ray emitted in the form of a cone beam from the X-ray source 11 passes through vicinity of the heart part. Then the instruction to start pre-radiographing is given by operating the operating section 23 of the console for radiography 20.

In response to the operation for the start of pre-radiographing, the control section 21 provides various controls for pre-radiographing. As shown in FIG. 6, as viewed from the top, 0 degree is assumed as the rotation angle phase wherein the surface of the detector 12 is parallel to the long axis 1w of the body portion of the subject W. Rotation is given by the drive section 17 in increments of 5 through 10 degrees within the range of the average rotation angle phase wherein the long axis 1b of the heart part "h" is approximately parallel to the surface of the detector 12 (e.g., 20 through 45 degrees). The control section 21 allows the X-ray source 11 to emit X-rays at every turn and permits the reading section 16 to read the X-ray image from the detector 12 at every emission. Also in the pre-radiographing mode, radiographing is preferably performed at approximately the same phase timing synchronized with heart beat.

The X-ray images having been read are sequentially inputted into the control section 21. The control section 21 analyzes the X-ray images in a plurality of rotation angle phases, and specifies the rotation angle phase wherein the long axis 1a of the heart part "gh" in the X-ray image "g" (FIG. 5) is maximized.

In analysis, the image area of the heart part "gh" is detected from the X-ray image "g". The heart part "gh" of the X-ray image "g" commonly appears in the form shown in FIG. 5. For example, a filter for detecting the edge of the area of the heart part "gh" is prepared and the X-ray image "g" having been obtained is subjected to a filtering process, whereby the area can be detected. It should be noted that there is no particular restriction to the method of the detection. Other methods can be used.

The control section 21 calculates the length in the main scanning direction of the X-ray image "g" in the area of the heart part "gh" having been detected. The maximum length is assumed to be the long axis 1a of the heart part "gh" of the X-ray image "g". The control section 21 obtains the long axis 1a in the X-ray image "g" of each rotation angle phase and specifies the X-ray image "g" of the long axis 1a to be the maximum length. The rotation angle phase of the X-ray image "g" having been specified is determined as the rotation angle phase at the second oblique position in which the dynamic radiographing is performed. (This is determined as the rotation angle phase in the actual radiographing mode in the second embodiment to be described later).

Figure 7:
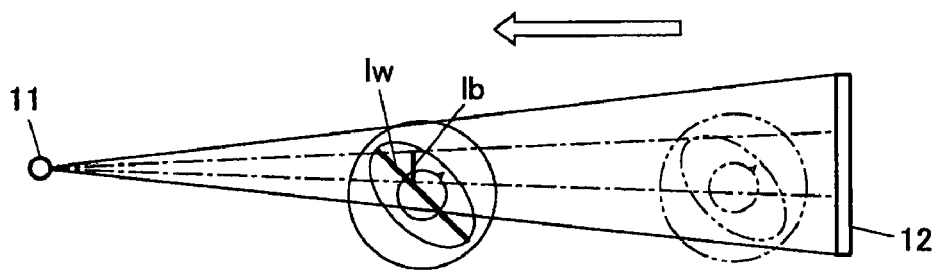
FIG. 7 is a diagram representing the relationship among the X-ray source, subject and detector in the dynamic radiographing mode.

When the rotation angle phase in the second oblique position has been determined, the radiographing apparatus 10 starts dynamic radiographing operation. The control section 21 controls the drive section 17 and rotates the holding section 13 to the rotation angle phase having been determined, whereby the holding section 13 is fixed in position. With that rotation angle phase kept unchanged, the control section 21 allows the drive section 17 to move the holding section 13 toward the X-ray source 11, as shown in FIG. 7. This is intended to start a magnification radiographing operation.

Magnification radiographing can be defined as the method of radiographing using a certain distance placed between the subject W and detector 12. In this method, the X-ray emitted in the form of a cone beam from the X-ray source 11 passes through the subject W. After that, the X-ray still continues to be in the form of a cone beam to enter the detector 12. Thus, the X-ray image having been obtained is enlarged as compared to the life size (actual size of the subject W). The image of this enlarged size is called the enlarged image.

The magnification rate M of the enlarged image with respect to the life size can be calculated from the following formula (1) wherein R1 denotes the distance from the X-ray source 11 to the subject W, R2 indicates the distance from the subject W to the detector 12, and R3 (=R1+R2) (unit of R1, R2 and R3 is m) represents the distance from the X-ray source 11 to detector 12:

$$M = R3/R1 \quad (1)$$

The magnification rate M can be adjusted by changing the distances R1 and R2.

In the magnification radiographing, it is possible to use the phase contrast radiographing wherein the edge enhancement effect on the margin of the subject W can be obtained by keeping the R1, R2 and R3 and the focal diameter of the X-ray source 11 within prescribed ranges, as disclosed in the Japanese Unexamined Patent Application Publication No. 2001-91479. The setting examples include the focal diameter D of 30 (μm) or more, R1 of (D-7)/200 or more, and R2 of 0.15 or more.

Figure 8:
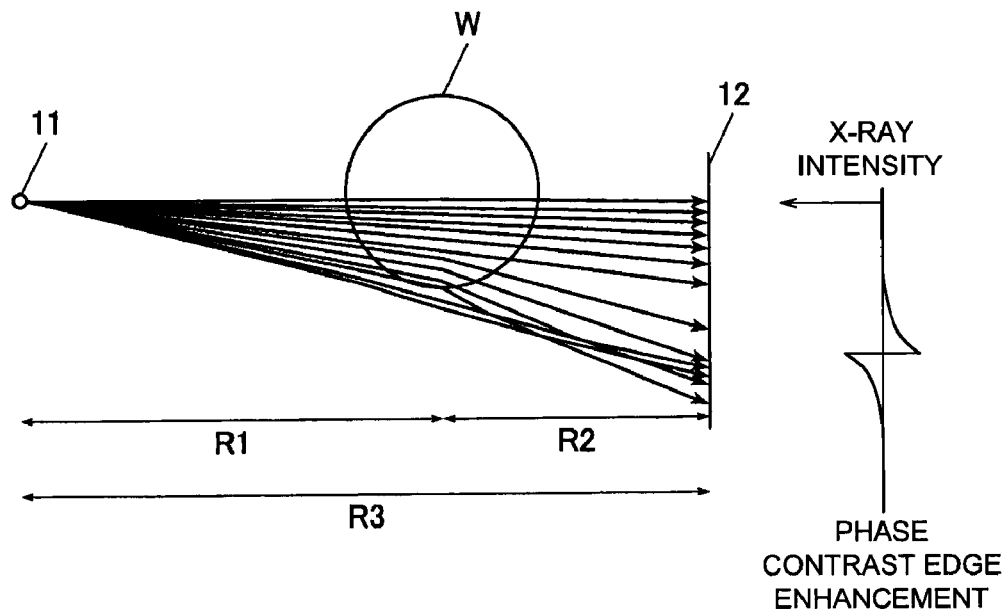
FIG. 8 is a diagram describing the edge effect in the phase contrast radiography.

In the phase contrast image obtained by the phase contrast radiographing, the X-ray having been refracted by passing through the margin of the subject W is overlapped with the X-ray having been sent without passing through the subject W, as shown in FIG. 8, with the result that the X-ray of the overlapped portion is intensified. In the meantime, the intensity of the X-ray is reduced at the portion inside the margin of the subject W due to the X-ray having been refracted. This activates the edge enhancement effect (also called the edge effect) wherein the difference in the X-ray intensity is increased with the margin of the subject W as a boundary. This will provide a highly visible X-ray image in which the marginal portion is clearly visible. Thus, the traveling distance of the holding section 13 can be set as appropriate, with consideration given to the magnification rate M and the edge effect in the phase contrast radiographing.

After the holding section 13 has completed the movement, the control section 21 conducts controls for dynamic radiographing. In the first place, the control section 21 allows the X-ray source 11 to emit X-rays. The X-ray irradiation requirements in this case include a tube current of 25 mA and a frame rate of 30 fps (30 frames/sec.) or more. The X-ray image corresponding to at least one cycle of beat or more should be collected. The frame interval is 1 through 2 seconds in conformance to the heart beat cycle. Due to a high frame rate, the dosage is slightly increased, with consideration given to the S/N ratio.

To enhance the contrast of the heart part in the X-ray image, the control section 21 reduces the tube voltage. Generally, when the chest including the lung field is to be radiographed, the tube voltage is normally set to about 120 kV. In this embodiment, though, the tube voltage is set to about 60 through 80 kV to gain the low-power. Since the heart part is radiographed, the subject need not suspend breathing at the time of radiographing.

Further, the control section 21 allows the reading section 16 to read the X-ray image from the detector 12, synchronously with X-ray irradiation. The reading requirements, for example, include a pixel size of 400 μm and an image size of 512×384 pixels. The control section 21 allows reading to be performed at every irradiation of the X-ray. Thus, the X-ray images (frame images) in a plurality of time phases are read from the reading section 16.

Since there is some distance between the subject W and detector 12, radiographing is performed as the magnification radiographing (or phase contrast radiographing) mode. Since the position of the subject W is fixed so that the heart part of the subject W will come to the center of the surface of the detector 12 at the time of pre-radiographing, the X-ray image obtained by dynamic radiographing should be the image with the heart part being enlarged, differently from the X-ray image including the entire chest part in the pre-radiographing. To be more specific, the X-ray image includes the lung field in addition to the heart part in the pre-radiographing mode. However, in the dynamic radiographing, the part of the lung field captured in the X-ray image is reduced and the heart part accounts for the major portion of the image. This arrangement is better suited to the diagnosis of the heart part.

The control section 21 provides control in such a way that the X-ray image at each time phase obtained by dynamic radiographing is displayed on the display section 24 for checking. In this case, the X-ray images are switched and displayed in conformance to each time phase on a continuous basis so that the dynamic state for one heart beat cycle can be checked. The radiographing technician checks the X-ray image in each time phase displayed thereon. If the image is satisfactory, the radiographing technician performs the operation of terminating the radiographing. In response to this operation, the control section 21 sends the group of X-ray images in respective time phases obtained by dynamic radiographing to the console for diagnosis 30 through the communicating section 25.

Similarly, the console for diagnosis 30 allows a group of X-ray images in respective time phases to be displayed for checking (Step S2). When the doctor has performed the operation of checking, the console for diagnosis 30 displays the operation screen for designating the ROI (area of interest to be diagnosed by the doctor) in the X-ray image of any one of the time phases. The doctor performs the operation of designating as ROI the area including the heart part and main artery part in the X-ray image.

When the blood speed, cardiac output and beat are to be evaluated, the main artery part is the ROI. In the meantime, the heart part is the ROI when evaluating the distance, directionality or periodicity of the movement of the local part of heart. Since the evaluation requires the segment of the heart part to be specified, the doctor specifies the segment in the heart part.

When the ROI and segment of the heart part have been specified, the console for diagnosis 30 generates the information on the specified position of the ROI and segment of the heart part as the ROI designation information. The group of the X-ray images in respective time phases together with the ROI designation information is sent to the image processing apparatus 40 through the network N (Step S3).

After applying image processing to the X-ray image in each time phase by means of the image processing section 46, the image processing apparatus 40 allows the image analysis section 47 to analyze images by using the X-ray image of each time phase, and calculates the evaluation value for heart function with regard to the blood speed, cardiac output and beat, and the distance, directionality or periodicity of the movement of the local part of heart (Step S4).

The evaluation value having been calculated is displayed on the console for diagnosis 30, and the X-ray images in each time phase are switched and displayed in conformance to each time phase on a continuous basis (Step S5).

The following describes the method of calculation.

[Evaluation Value of Blood Speed and Cardiac Output]

Figure 9:
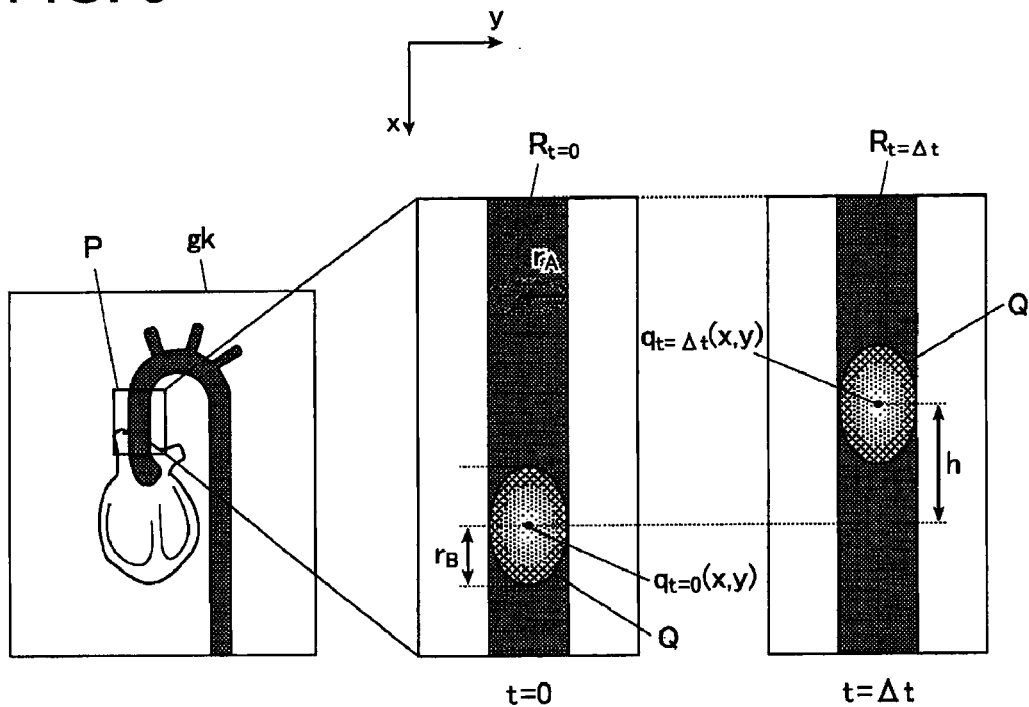
FIG. 9 is a diagram describing the method of calculating the blood speed and cardiac output.

FIG. 9 shows the X-ray image "gk" obtained by dynamic radiographing. The X-ray image "gk" shows an enlarged view of the heart part taken by magnification radiographing (or phase contrast radiographing). The image analysis section 47 detects the main artery area R specified as ROI in the X-ray image "gk" in each time phase, based on the ROI designation information. The ROI has been specified in the X-ray image for a certain time phase. The positions of the heart part and main artery specified as ROIs are considered as being approximately the same, although the time phases are different. The ROIs specified for a certain time phase are applied to all the X-ray images of time phases.

Assuming that "t" denotes time phase, the image $R_{t=0}$, $R_{t=\Delta t}$ of FIG. 9 shows the enlarged view of the image portion of the area P of the X-ray image "gk" in time phase t=0, Δt.

The pumping function of the heart can be regarded as sending the lump of blood to the main artery in a simulated manner. Thus, the traveling distance of the lump of blood per unit time can be obtained as the blood speed, and the volume can be obtained as the cardiac output.

The image analysis section 47 detects the part of the lump of blood (hereinafter referred to as "pulsation part") pushed out from the heart part in the image R. The pulsation part has a higher density than that of other blood portions. The image should be represented as a low signal value. Accordingly, the image analysis section 47 creates the histogram of the signal values for images $R_{t=0}$, $R_{t=\Delta t}$, and detects from this histogram the area that will generally exhibit low signal values. To put it more specifically, two peaks showing the pulsation part and other blood flow part are considered to appear on the histogram. The peak value for lower signal value is assumed to belong to the pulsation part. As shown in FIG. 9, the area having the signal value near the peak value assumed to belong to the pulsation part in the images $R_{t=0}$, $R_{t=\Delta t}$ is detected as the pulsation part Q.

Then the image analysis section 47 finds out the position of the gravity centers $q_{t=0}$, $q_{t=\Delta t}$ of the pulsation part Q in the images $R_{t=0}$, $R_{t=\Delta t}$ of different time phases. The position is found out in terms of the x and y coordinates when x indicates the number of pixels in the main scanning direction and y denotes the number of pixels in the auxiliary scanning direction of images $R_{t=0}$, $R_{t=\Delta t}$.

When the position of gravity center has been obtained, the image analysis section 47 detects the traveling distance "h" of the gravity centers $q_{t=0}$, $q_{t=\Delta t}$ between the images $R_{t=0}$, $R_{t=\Delta t}$, and calculates the traveling distance "h" per unit time, i.e., the evaluation value E1 of blood speed from the time $\Delta t$ between the images $R_{t=0}$, $R_{t=\Delta t}$. The evaluation value E1 of the blood speed can be expressed by the following formula 2.

$$E1 = h/\Delta t \qquad (2)$$

When the pulsation part Q is assumed to be elliptical, the cardiac output can be regarded as the volume of an ellipse. Assuming that the cross section of the vessel of the main artery is circular, the volume of the pulsation part Q can be obtained from the radius $r_A$ of the blood vessel and radius $r_B$ of the long axis portion of the pulsation part Q. Thus, the image analysis section 47 obtains the radiuses $r_A$, $r_B$ in any of the images $R_{t=0}$, $R_{t=\Delta t}$, and calculates the evaluation value E2 for the cardiac output therefrom according to the following formula 3.

$$E2 = 4\pi r_B \times r_A^2 / 3 \qquad (3)$$

The blood vessel of the main artery can be detected by filter processing using a Sobel filter for detecting the edge of this vessel, and half the distance between the edges of the blood vessel is calculated as the radius $r_A$ of the blood vessel. Further, the radius $r_B$ can be obtained by getting the length of the pulsation part Q in the auxiliary scanning direction, and halving this length.

[Evaluation Value for Beat]

Figure 10:
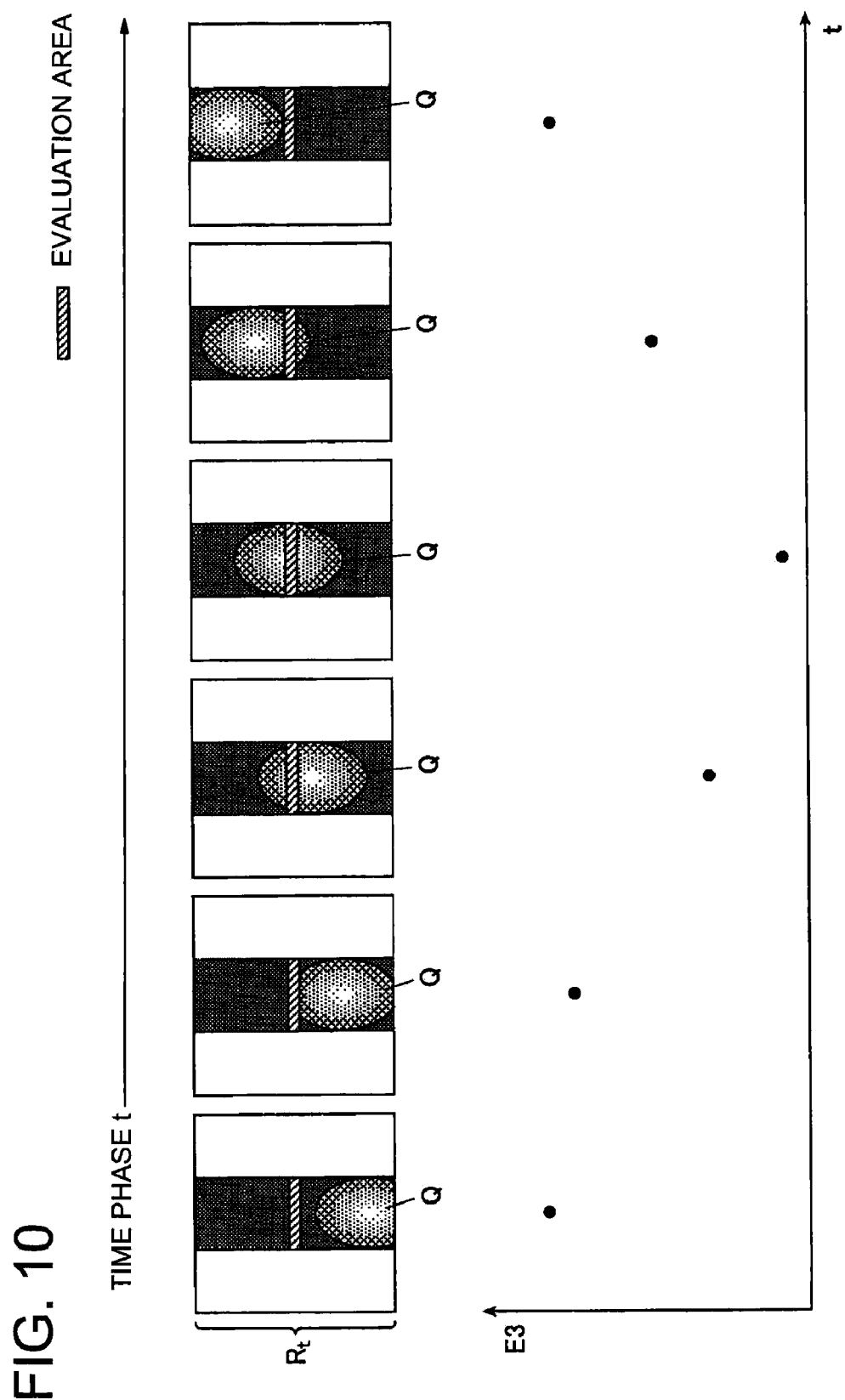
FIG. 10 is a diagram describing the method of calculating the evaluation value for beat.

The evaluation value for beat is an indicator showing the amount of change in the signal value of the image in a certain area of the blood vessel of the main artery. For example, as shown in FIG. 10, when there are images $R_t$ of the main artery part identified from the X-ray images in a plurality of time phases, the evaluation area (area indicated by oblique lines in FIG. 10) is set so that the main artery is crossed by the evaluation area at the same position of each image $R_t$. The average value of the signal values within this evaluation area is obtained as the evaluation value E3 of the beat. The method of detecting the main artery is as described above.

As shown in FIG. 10, the position of the pulsation part Q varies with changes in time phase "t". Since the pulsation part Q has a lower signal value than that of other blood flow part, the signal value within the evaluation area varies according to the traveling of the pulsation part Q. Thus, the evaluation value E3 is gradually reduced in the process of the pulsation part Q entering the evaluation area, and is gradually increased in the process of the pulsation part Q moving away from the evaluation area. The change in the evaluation value E3 is repeated at every feeding of the blood out of the heart, i.e., in conformance to the beat cycle. Accordingly, the beat can be identified by referring to the evaluation value E3.

[Distance, Directionality or Periodicity of the Movement of Local Part of Heart]

The evaluation value for the movement of the local part of heart is calculated from the optical flow.

The image analysis section 47 identifies the image of the heart part from the X-ray images in each time phase based on the ROI designation information, and calculates the optical flow on each image of the heart part having been detected. The optical flow can be defined as the movement of the target on the image with the lapse of time, locally analyzed and represented in terms of velocity vector. The optical flow can be calculated between the X-ray images of consecutive time phases. Alternatively, an X-ray images in any particular time phase is determined as a reference, and the optical flow can be calculated between this reference X-ray image and other X-ray images. Further, calculation can be made in any method such as a gradient method and block matching method.

Figure 11:
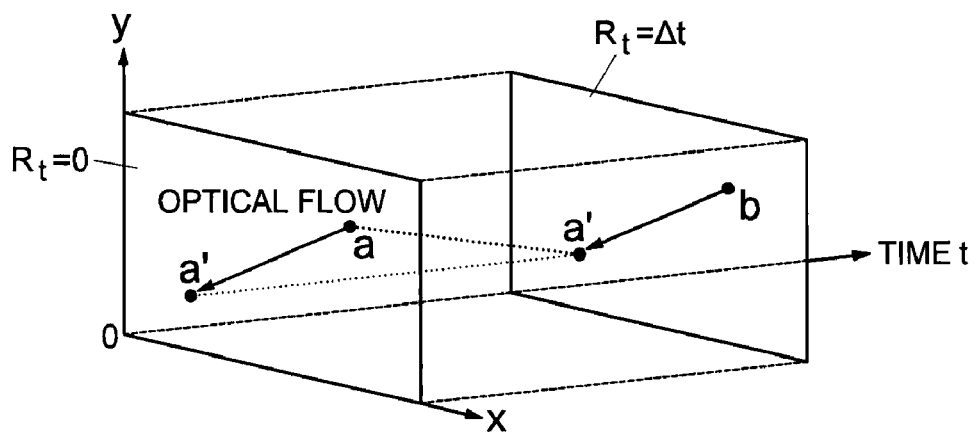
FIG. 11 is a diagram describing the method of calculating the evaluation value for movement of the local part of heart.

FIG. 11 shows the example of calculating the optical flow.

FIG. 11 is a diagram showing the result of calculating the optical flow calculated between the images $R_{t=0}$, $R_{t=\Delta t}$ of the heart part identified from the X-ray images in the time phases t=0, t=$\Delta t$. It is an example of studying the movement of the target point "a" ("a" denotes a pixel) related to the heart part in the image $R_{t=0}$. Assuming that "a'" denotes the point in the image $R_{t=\Delta t}$ corresponding to this target point "a", a step is taken to calculate the velocity vector showing the movement from "a" to "a'" in the image $R_{t=0}$. The size of the arrow of this velocity vector indicates the traveling distance of the target point "a", and the direction of the arrow shows the directivity. The velocity vector for each time phase for calculating the optical flow represents the evaluation value for the periodicity of the traveling distance and directionality of the target point "a".

Further, the image analysis section 47 identifies the segments in the heart part based on the ROI designation information, and calculates the average value of the optical flow in chronological order for each of these segments and the periodicity of the average value thereof. The results of calculation are used as the evaluation values for the traveling distance and directionality, and the evaluation value for the periodicity in units of segments. As described above, the evaluation value obtained for each segment of the heart part provides valuable information for diagnosis. The heart function reduction is not caused by the reduction in the function of the entire heart by the angina or heart infarction, but by the reduction in the function of the heart part controlled by the constricted or blocked coronary artery. Thus, partial evaluation is important.

The segments can be the major units of a left ventricle, left atrium, right ventricle and right atrium, or the minor units of an interventricular septum, cardiac apex, paries anterior, paries posterior and panes inferior in the left ventricle. As described above, the doctor designates the heart part and segment as the ROIs in the console for diagnosis 30. Thus, the image analysis section 47 identifies the heart part and segment based on the ROI designation information.

Upon termination of the aforementioned analysis, each of the evaluation values for the heart function as the results of image analysis is attached to the group of the X-ray images in each time phase under the control of the control section 41, and is sent to the server 50. The server 50 stores the information on evaluation value together with the group of the X-ray images. After that, in response to the request of the X-ray image through the console for diagnosis 30, the group of the X-ray images in each of the time phases and the evaluation value for heart function are sent to the console for diagnosis 30 from the server 50.

The console for diagnosis 30 displays the group of the X-ray images in each time phase under the control of the control section. The information on the evaluation value for heart function as the result of image analysis is also displayed on the display section. The X-ray images are displayed as dynamic images when the X-ray images in each time phase are switched and displayed in response to the time phase on a continuous basis.

Figure 12:
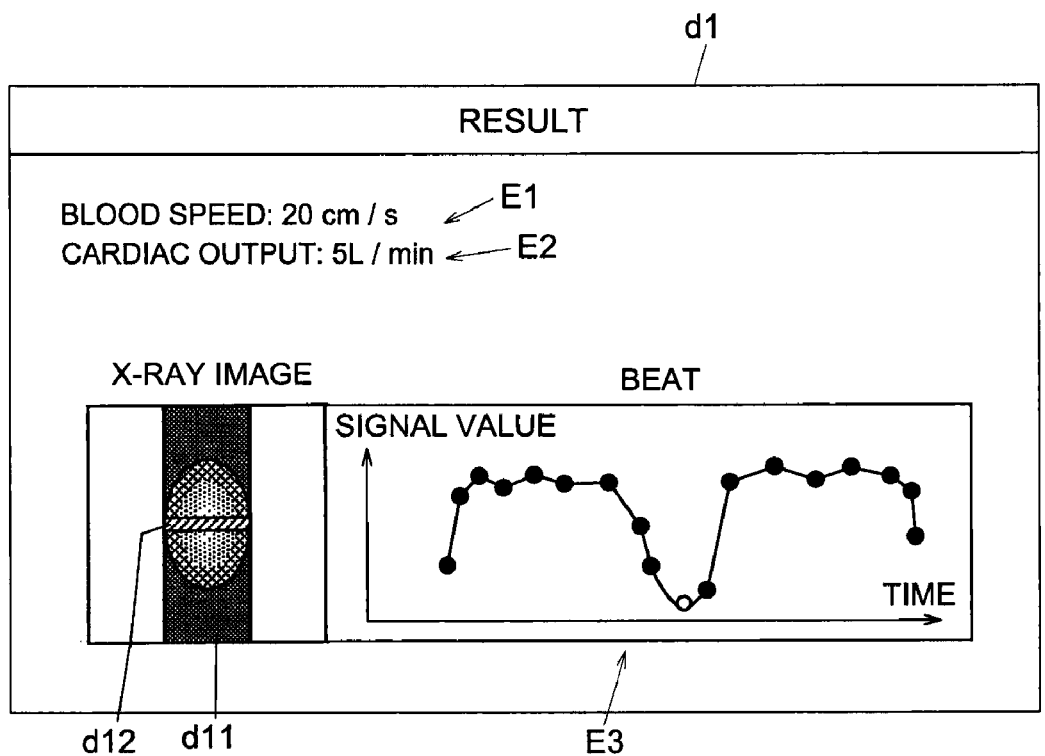
FIG. 12 is a diagram representing the display examples of evaluation values for the blood speed, cardiac output and beat.

FIG. 12 gives a display screen d1 showing the blood speed, cardiac output and beat as an example of the evaluation value.

As shown in FIG. 12, the evaluation value E1 of the blood speed and the evaluation value E2 of the cardiac output are shown on the display screen d1.

The lower portion of the display screen d1 also shows the area d11 showing the group of the X-ray images for calculating the evaluation value, and the evaluation value E3 for the beat calculated from each of the X-ray images.

In the area d11, the X-ray images are switched and displayed on a continuous basis in response to the time phase. The pulsation part has a different brightness from other blood flow parts. This allows the doctor to identify the dynamic change of the pulsation part by switching and displaying. The X-ray image is shown to provide reference for the evaluation value. There is no need of displaying all the X-ray images of time phases. It is only required that any one of them is displayed.

Further, each of the X-ray images is displayed in such a way that the image portion as the evaluation area can be identified. This is intended to show to the doctor which area is evaluated by the evaluation value E3. In FIG. 12, the image portion d12 shown by the oblique lines is the evaluated area.

In conjunction with the display of the area d11, the plot points of the evaluation value E3 calculated for the X-ray image being displayed in the area d11 are shown in white, while the plot points corresponding to other X-ray images are shown in black. This ensures the doctor to easily identify which of the evaluation values E3 corresponds to the X-ray image being currently displayed on the area d11.

Figure 13:
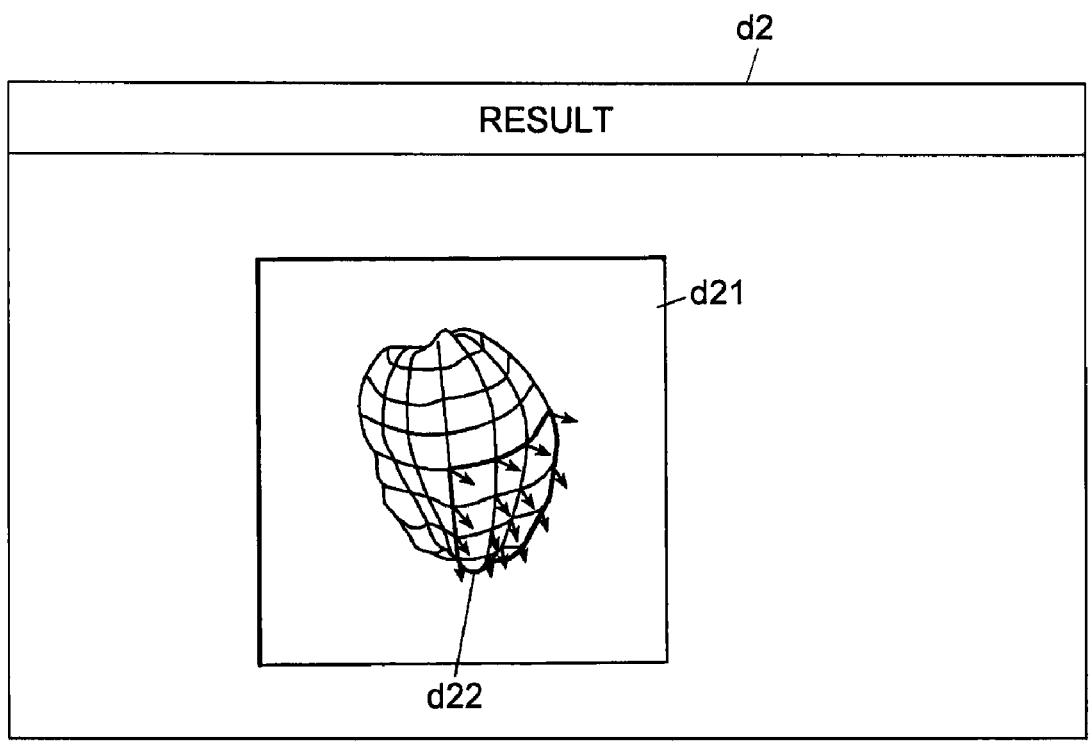
FIG. 13 is a diagram representing the display examples of evaluation values for movement of the local part of heart.

FIG. 13 shows the example of displaying the distance, directionality and periodicity of the movement of the local part of heart.

The display screen d2 of FIG. 13 shows the image d21 in which the heart part is extracted. In this image d21, the vector (indicated by an arrow in FIG. 13) showing the distance and directionality of the movement at the target point on the heart part is shown as the evaluation value. The vector is switched and displayed on a continuous basis for each time phase where the optical flow has been calculated, whereby the periodicity is illustrated. It is also possible to make such arrangements that the X-ray image in each time phase is displayed in the display screen d2.

The vector is displayed in units of segments designated by the doctor. Only the image portion d22 of the segment designated by the doctor in the image d21 is displayed, for example. If the operation for display instruction has been made by the doctor, the vector representing the average of the traveling distance and directionality calculated in units of segments is displayed. Further, the periodicity of the average value is displayed by continuously switching and displaying for each time phase.

As described above, according to the present embodiment, the X-ray images in a plurality of time phases are generated by dynamic radiographing in the radiographing apparatus 10. In the image processing apparatus 40, the evaluation value for heart function is calculated using these X-ray images. This arrangement ensures the doctor to get the evaluation value for heart function for diagnostic use by plain X-ray radiographing operation. This can be achieved by using a widely used radiographing apparatus 10 for plain X-ray radiographing operation, without having to use a high-priced imaging apparatus such as an MRI, whereby cost reduction can be accomplished. As the evaluation values for heart function, both the blood-related evaluation values for blood speed, cardiac output and beat, and the evaluation value for the movement of the heart, can be calculated with plain X-ray radiographing operations often performed in a basic manner. This method eliminates the need of examining the blood flow and heart part separately, with the result that the patient burden is reduced.

For the evaluation value for heart function, the image of the pulsation part is detected from the X-ray image, and the blood speed is calculated from the traveling distance of the gravity center of this image. This allows the doctor to evaluate the blood speed. Further, the cardiac output is calculated from the volume of the pulsation part, and the doctor can evaluate the cardiac output.

Further, the images of the main artery are detected from the X-ray images in a plurality of time phases, and changes in the signal value in a certain area of the main artery part are calculated as the evaluation value for beat. This permits the doctor to evaluate the beat.

The image of the heart part is detected and the optical flow of this image is calculated, whereby the evaluation values for the distance, directionality and periodicity of the movement of the local part of heart are calculated. Thus, the doctor can evaluate the distance, directionality and periodicity of the movement of the local part of heart.

The evaluation values having been calculated are displayed on the console for diagnosis 30, and the X-ray images in each time phase are switched and displayed in response to the time phase on a continuous basis. Then the doctor can evaluate the heart function while observing the dynamic changes in the heart part.

Dynamic radiographing is performed by a magnification radiographing method, which provides the X-ray image in which the heart part is enlarged. This can supply the doctor with the X-ray image suited for diagnosis of the heart part.

Further, dynamic radiographing is performed after preradiographing has been performed to specify the rotation angle phase where the long axis of the heart part in the X-ray image is the longest. This allows the radiographing operation to be performed in the direction suited for observation of the heart part and evaluation of the heart function.

It should be noted that the aforementioned embodiment provides an example preferably used in the present invention, without the present invention being restricted thereto.

For example, in the aforementioned embodiment, the ROI is designated by the doctor. It is also possible to adopt an automatic detection structure in such a way that a template for ROI detection is prepared in advance in the image processing apparatus 40, and template matching is performed.

In the above description, evaluation values are displayed on the console for diagnosis 30. These evaluation values can also be displayed on the console for radiography 20 and other apparatuses (for example, PC used for diagnosis). Further, in the above description, an image processing apparatus 40 capable of image analysis is provided to get the evaluation values calculated by this image processing apparatus 40. It is also possible to adopt such a configuration that a program for image analysis is installed in the console for diagnosis 30 and other apparatuses, whereby evaluation values are calculated.

In addition to the memory such as a ROM, a portable medium such as a DVD can also be used as the computer-readable medium for storing the program related to the aforementioned processing. Further, the carrier wave can also be used as the medium for providing the program data via the network.

The Second Embodiment

Figure 14:
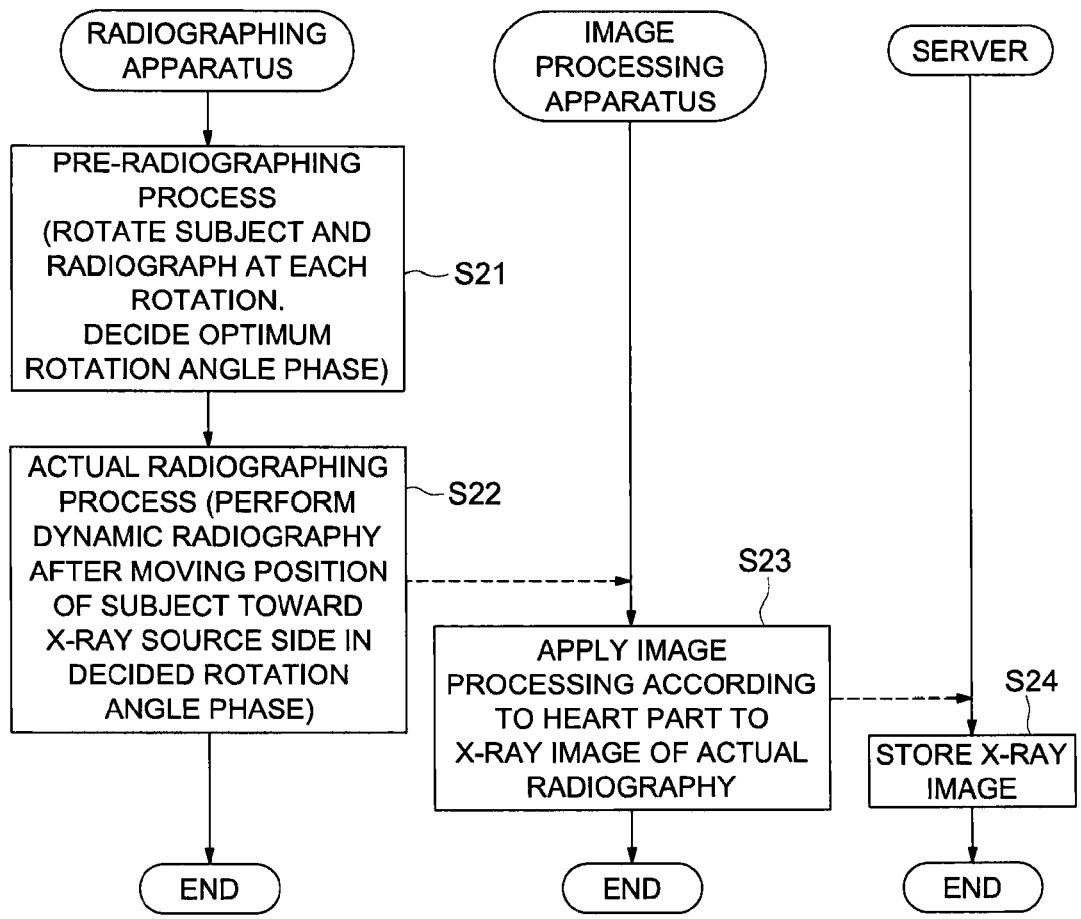
FIG. 14 is a diagram representing a flow of processing in the second embodiment.

When radiographing the heart part, the dynamic radiographing system 1 in the second embodiment allows pre-radiographing to be performed, with the holding section 13 moved on the side of the detector 12 in the radiographing apparatus 10, and determined the optimum rotation angle phase of the holding section 13. In the actual radiographing mode, the holding section 13 is fixed at the rotation angle phase having been determined and the holding section 13 is moved toward the X-ray source 11, whereby phase contrast radiographing is performed. FIG. 14 shows the flow of processing of the radiographing apparatus 10, image processing apparatus 40 and server 50 in the radiographing system 1 in the second embodiment. The structure of the dynamic radiographing system 1 in the second embodiment is the same as that already described with reference to FIGS. 1 through 3, and will not be described.

As shown in FIG. 14, pre-radiographing is performed in the radiographing apparatus 10 (Step S21). The pre-radiographing is intended to specify the radiographing direction that ensures easy observation of the heart part, and the rotation angle phase of the holding section 13 is fixed in position so that radiographing can be performed in that direction.

The same processing as that of the first embodiment is performed (FIGS. 5 through 8), whereby the control section 21 calculates the length of the X-ray image "g" in the main scanning direction in the area of the heart part "gh" having been detected. The maximum length is determined as the long axis 1a in the heart part "gh" of the X-ray image "g". The control section 21 calculates the long axis 1a with respect to the X-ray image "g" of each rotation angle phase and specifies the X-ray image "g" with the longest axis 1a out of the long axes 1a having been obtained. The rotation angle phase of the X-ray image "g" having been specified is determined as the rotation angle phase in the actual radiographing mode.

When the rotation angle phase in the actual radiographing mode has been determined, the radiographing operation is performed by the radiographing apparatus 10 (Step S22). This operation is a dynamic radiographing operation. In this radiographing, the control section 21 controls the drive section 17, whereby the holding section 13 is rotated to the determined rotation angle phase and fixed. Further, with the rotation angle phase kept unchanged, the control section 21 allows the holding section 13 to be moved toward the X-ray source 11 by the drive section 17, as shown in FIG. 7. This is intended to apply the aforementioned magnification radiographing or the phase contrast radiographing that ensures the edge enhancement effect of the margin of the subject W.

The control section 21 ensures that the group of X-ray images in each time phase obtained by the radiographing is displayed on the display section 24 for the sake of checking. In this case, the X-ray images are switched and displayed on a continuous basis in response to each time phase, whereby the dynamic state for one heart beat cycle can be checked. The radiographing technician checks the X-ray image in each time phase having been displayed and performs the operation of completing the radiographing if the result of checking is satisfactory. In response to this operation, the control section 21 sends to the console for diagnosis 30 the group of X-ray images in each time phase obtained by the radiographing through the communicating section 25.

Similarly to the aforementioned case, the console for diagnosis 30 displays the group of X-ray images in each time phase so as to be checked. If the doctor has operated to give an instruction indicating that the displayed status is satisfactory, the group of X-ray images in each frame is sent to the image processing apparatus 40 from the console for diagnosis 30.

In the image processing apparatus 40, the image processing section 46 applies various forms of image processing to the group of X-ray images in each frame. The image processing is provided in such a way that the heart part can be easily examined in conformity to the heart part. In the following description, the examples will be taken from the processing of normalization and gradation conversion.

In the processing of normalization, the maximum signal value H or the minimum signal value L are obtained from the histogram of the signal value of the X-ray image, and these signals are converted to agree with the prescribed reference signals SH and SL. This corrects the variation of the reached X-ray dosage produced by the variations in the body shape of the subject W and X-ray irradiation conditions.

In the processing of gradation conversion, the density and contrast in image output are adjusted. A basic LUT (Look-Up Table) is used to convert the signal values so as to get a desired gradation characteristics.

Figure 15:
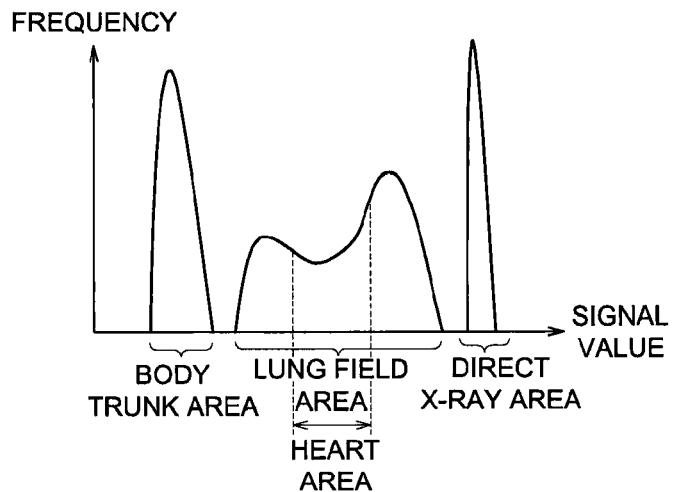
FIG. 15 is a histogram of the signal value in the X-ray image.

FIG. 15 is a histogram of the signal value in the X-ray image obtained by radiographing the chest part. In the histogram, different characteristics appear according to different radiographed positions. In the histogram of FIG. 15, the peak appearing in the area of low signal value represents the signal of the body trunk area, and the peak appearing in the area of high signal value indicates the direct X-ray area wherein X-rays are directly detected. The two peaks appearing between these two peaks show the signal values of the lung field area.

The range indicated by an arrow in the signal values of the lung field area often indicate the signal values of the heart part. In the present embodiment, gradation conversion is performed in such a way as to increase the contrast of the range of these signals.

Figure 16:
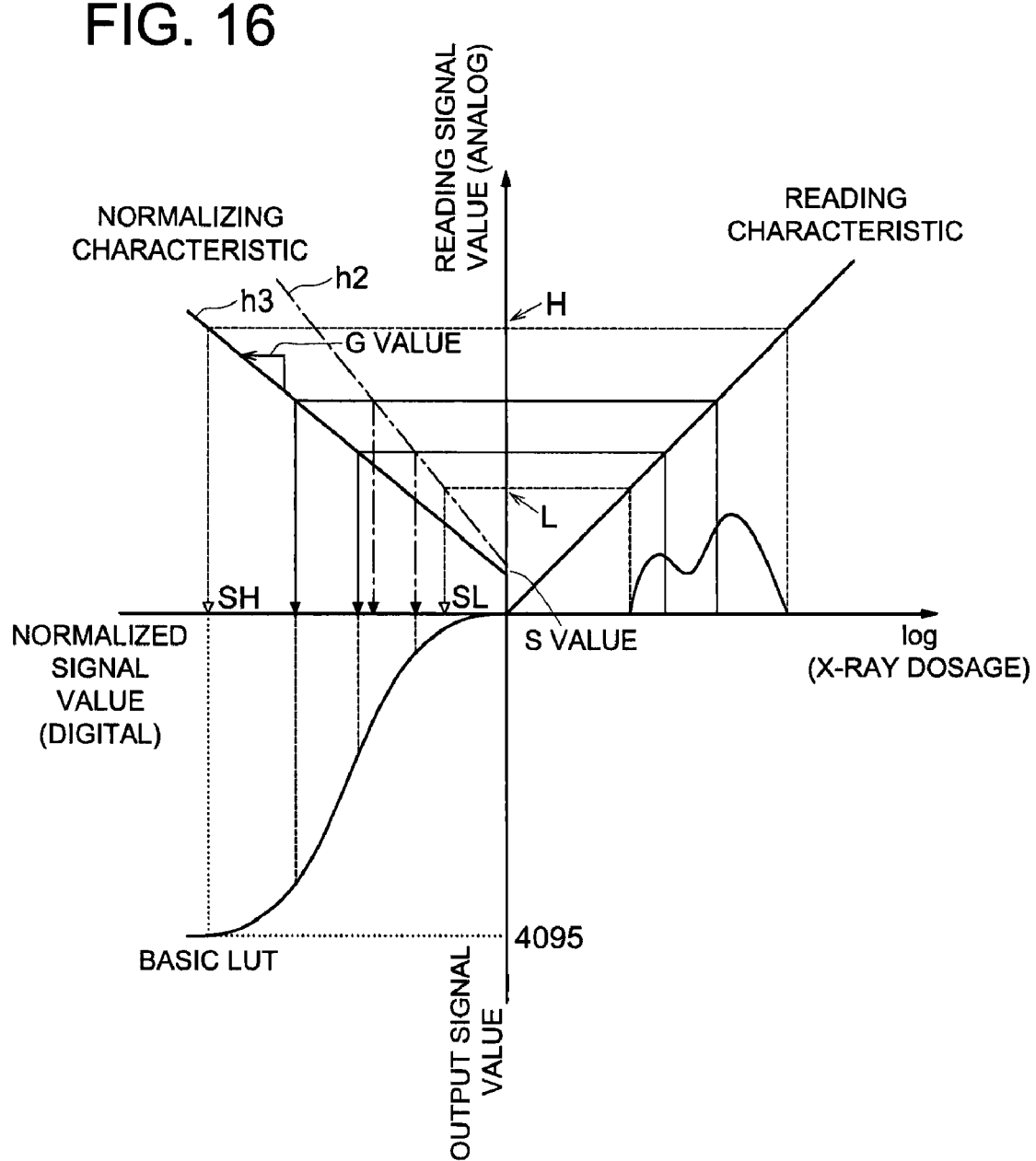
FIG. 16 is a diagram representing the normalizing characteristics in the process of normalizing applied to the X-ray image and the conversion curve used in the process of gradation conversion.

FIG. 16 shows the relationship between the X-ray dosage detected by the detector 12 and the signal value of the X-ray image finally outputted in response to the X-ray dosage.

In the coordinates of FIG. 16, the first quadrant shows the reading characteristics. It indicates the relationship between the X-ray dosage reaching the detector 12 and the reading signal value (analog signal value). The second quadrant shows the normalizing characteristics. It represents the relationship between the reading signal value and normalized signal value subsequent to the processing of normalization. The third quadrant shows the gradation characteristics. It represents the relationship between the normalized signal value and the output signal value (digital signal value) having been converted with the basic LUT. To be more specific, the basic LUT used in the processing of gradation conversion is the tabulated form of the conversion curve shown in the third quadrant. It should be noted that the output signal value is given in a 12-bit resolution of 0 through 4095 in this case.

In the second quadrant, the range of the output (the measures between SH and SL in FIG. 16) can be adjusted by changing the inclination of the straight line showing the normalizing characteristics. Further, the contrast of the entire image can be changed. The inclination of this straight line is called the value G. The height (travel of the range between SH and SL) of the entire range of the output value can be adjusted by changing the segment end of the straight line showing the gradation conversion characteristics. Accordingly, the density of the entire image can be changed. This segment end is referred to as the value S.

For example, comparison is made regarding the cases where normalization has been achieved using the straight line h2 and straight line h3 of FIG. 16. When there is an increase of the value G, the normalized signal value corresponding to the heart part corresponds to the straight line area of the basic LUT. This can improve the contrast of the heart part. By changing the value (the area with large transmitted X-ray dosage reaches the saturated state. However, this area is not the target of radiographic interpretation, and no problem arises.

The image processing section 46 adjusts the density range and contrast of the X-ray image in each time phase by changing the values G and S representing gradation conversion characteristics and sets the values G and S so that the contrast of the heart part will be increased.

The image processing apparatus 40 applies required image processing in addition to the aforementioned processing of gradation conversion to the X-ray image in each time phase (Step S23), and sends to the server 50 the group of the X-ray images in each frame having been subjected to image processing. The server 50 organizes the group of the X-ray images in each time phase into a database and stores this database (Step S24).

As described above, in the present embodiment, pre-radiographing is performed to specify the rotation angle phase where the long axis of the heart part is the longest. Then radiographing is performed at the rotation angle phase. This ensures radiographing to be performed from the direction that permits easiest observation of the dynamic status of the heart, whereby an X-ray image suited for diagnosis can be obtained. Further, radiographing is performed by the radiographing apparatus 10 based on the normal plain X-ray radiographing method. This means a reduced burden on the patient. The radiographing apparatuses 10 based on a plain X-ray radiographing method are widely used in the medical institutions. Without having to introduce a new CT radiographing apparatus, the X-ray image suited for diagnosis of the heart can be obtained using the conventional radiographing apparatus 10. This contributes to cost reduction.

In the actual radiographing mode, dynamic radiographing is performed. Thus, at the time of medical examination, the X-ray images in each time phase obtained by dynamic radiographing are switched and displayed on a continuous basis. This allows moving images to be observed. Thus, the behavior of the blood flow and others in the heart can be checked at the time of medical examination.

Further, at the time of the radiographing, the holding section 13 is moved toward the X-ray source 11, and magnification radiographing is performed. This provides the X-ray image with an enlarged view of the heart part. Thus, the doctor is supplied with the X-ray image ensuring easier observation of the heart part. Phase contrast radiographing can be performed by adjusting the radiographing conditions at the time of this radiographing. Use of this phase contrast radiographing mode provides a high-quality X-ray image characterized by a clear view of the edge portion of the tissue of the heart part, in addition to enlarged view of the heart part.

In the image processing apparatus 40, image processing conforming to a heart part is applied to the X-ray image for the purpose of improving the contrast of the heart part. This provides a high-quality X-ray image suited for medical examination of the heart part.

It should be noted that the aforementioned embodiment is a preferred example of the present invention, without the present invention being restricted thereto.

For example, in addition to the memory such as a ROM, a portable medium such as a DVD can also be used as the computer-readable medium for storing the program used for the aforementioned processing. Further, a carrier wave can also be used as a medium for providing the program data via the network.

What is claimed is:

1. A dynamic radiographing system comprising:
a radiographing device which radiographs dynamically a heart part of a subject by plain radiography and generates X-ray images in a plurality of time phases, the radiographing device including
an X-ray source for emitting an X-ray and
a detector for detecting the X-ray emitted from the X-ray source;
an image analysis device for calculating an evaluation value relating to a heart function using the X-ray images in the plurality of time phases;
a display device; and
a control device which allows the display device to display thereon information on the calculated evaluation value
wherein the evaluation value includes an evaluation value of blood speed and
wherein the image analysis device detects images of a pulsating part from the X-ray images in the plurality of time phases, and calculates a center of gravity of the pulsating part detected from each of the X-ray images in the plurality of time phases, and then calculates a traveling distance of the center of gravity per unit time as the evaluation value of blood speed.

2. The dynamic radiographing system of claim 1,
wherein the control device allows the display device to display thereon at least one of the X-ray images in the plurality of time phases together with the information on the evaluation value.

3. A dynamic radiographing system comprising:
a radiographing device which radiographs dynamically a heart part of a subject by plain radiography and generates X-ray images in a plurality of time phases, the radiographing device including
an X-ray source for emitting an X-ray and
a detector for detecting the X-ray emitted from the X-ray source;
an image analysis device for calculating an evaluation value relating to a heart function using the X-ray images in the plurality of time phases;
a display device; and
a control device which allows the display device to display thereon information on the calculated evaluation value
wherein the evaluation value includes an evaluation value of cardiac output and
wherein the image analysis device detects an image of a pulsating part from the X-ray images in the plurality of time phases, and calculates a volume of the pulsating part having been detected as the evaluation value of cardiac output.

4. A dynamic radiographing system comprising:
a radiographing device which radiographs dynamically a heart part of a subject by plain radiography and generates X-ray images in a plurality of time phases, the radiographing device including
an X-ray source for emitting an X-ray and
a detector for detecting the X-ray emitted from the X-ray source;
an image analysis device for calculating an evaluation value relating to a heart function using the X-ray images in the plurality of time phases;
a display device; and
a control device which allows the display device to display thereon information on the calculated evaluation value
wherein the evaluation value includes an evaluation value of a beat and wherein the image analysis device detects images of a main artery part from the X-ray images in the plurality of time phases, and calculates a change of a signal value in a prescribed area of the main artery part detected from each of the X-ray images in the plurality of time phases as the evaluation value of the beat.

5. A dynamic radiographing system comprising:
a radiographing device which radiographs dynamically a heart part of a subject by plain radiography and generates X-ray images in a plurality of time phases, the radiographing device including
 an X-ray source for emitting an X-ray and
 a detector for detecting the X-ray emitted from the X-ray source;
an image analysis device for calculating an evaluation value relating to a heart function using the X-ray images in the plurality of time phases;
a display device; and
a control device which allows the display device to display thereon information on the calculated evaluation value
wherein the evaluation value includes an evaluation value of a distance, directionality or periodicity of a movement of a local part of heart and
wherein the image analysis device detects images of the heart part from the X-ray images in the plurality of time phases, and calculates the distance, the directionality or the periodicity of the movement of the local part of heart between the images of the heart part of different time phases.

6. The dynamic radiographing system of claim 5,
wherein the image analysis device calculates the evaluation value for the distance, the directionality or the periodicity of the movement of the local part of heart for each segment of the heart part.

7. A dynamic radiographing system comprising:
a radiographing device which radiographs dynamically a heart part of a subject by plain radiography and generates X-ray images in a plurality of time phases, the radiographing device including
 an X-ray source for emitting an X-ray and
 a detector for detecting the X-ray emitted from the X-ray source;
an image analysis device for calculating an evaluation value relating to a heart function using the X-ray images in the plurality of time phases;
a display device; and
a control device which allows the display device to display thereon information on the calculated evaluation value
wherein the radiographing device takes an enlarged radiograph of the heart part.

8. A dynamic radiographing system comprising:
a radiographing device which radiographs dynamically a heart part of a subject by plain radiography and generates X-ray images in a plurality of time phases, the radiographing device including
 an X-ray source for emitting an X-ray and
 a detector for detecting the X-ray emitted from the X-ray source;
an image analysis device for calculating an evaluation value relating to a heart function using the X-ray images in the plurality of time phases;
a display device; and
a control device which allows the display device to display thereon information on the calculated evaluation value
wherein the radiographing device radiographs in a rotation angle phase in which a long axis of the heart part in an X-ray image is longest.

9. The dynamic radiographing system of claim 8, further comprising:
a holding device which holds the subject which is a radiographing target rotatably between the X-ray source and the detector; and
a reading device for reading an X-ray image from the detector,
wherein the control device controls so that a rotation angle phase of the holding device is variable and the X-ray source emits an X-ray in a plurality of rotation angle phases in a pre-radiographing mode, and the control device determines a rotation angle phase in which a long axis of a heart area is longest, based on each of X-ray images obtained in each of the a plurality of rotation angle phases from the detector by the reading device, and allows the X-ray source to emit the X-ray while fixing the holding device at the rotation angle phase in an actual radiographing mode.

10. The dynamic radiographing system of claim 9,
wherein the holding device is arranged movably between the X-ray source and the detector and
wherein the control device determines the rotation angle phase in which the long axis of the heart area is longest at a position where the holding device has moved toward the detector in the pre-radiographing mode, and the control device allows the holding device to move toward the X-ray source after fixing the rotation angle phase of the holding device in the actual radiographing mode.

11. The dynamic radiographing system of claim 9,
wherein the control device allows the X-ray source to emit an X-ray a plurality of times continuously in the actual radiographing mode, and allows the reading device to read the X-ray image from the detector for each emission of the X-ray so as to allow the system to perform dynamic radiographing of the heart area.

12. The dynamic radiographing system of claim 9, further comprising:
an image processing device which applies image processing in conformity to the heart part to the X-ray image obtained by an actual radiographing operation.

* * * * *